United States Patent [19]
Nishiyama

[11] Patent Number: 5,720,394
[45] Date of Patent: Feb. 24, 1998

[54] SAMPLE SUPPLY UNIT FOR SETTLING CLASSIFICATION SYSTEM

[75] Inventor: Yugo Nishiyama, Susono, Japan

[73] Assignee: Yazaki Corporation, Tokyo, Japan

[21] Appl. No.: 498,496

[22] Filed: Jul. 5, 1995

[30] Foreign Application Priority Data

Jul. 15, 1994 [JP] Japan ................................ 6-163469

[51] Int. Cl.$^6$ ................................................ B03B 5/60
[52] U.S. Cl. ............................................ 209/172; 209/173
[58] Field of Search ................................ 209/155, 172, 209/172.5, 173

[56] References Cited

U.S. PATENT DOCUMENTS

| | | | |
|---|---|---|---|
| 4,657,668 | 4/1987 | Harsanyi et al. | 209/172 X |
| 4,714,553 | 12/1987 | Crouzet | 209/172 X |
| 5,246,116 | 9/1993 | Kirk | 209/173 X |

FOREIGN PATENT DOCUMENTS

| | | |
|---|---|---|
| 59-196760 | 11/1984 | Japan . |
| 3-99 | 1/1991 | Japan . |
| 3-178352 | 8/1991 | Japan . |
| 6-328002 | 11/1994 | Japan . |

*Primary Examiner*—Tuan Nguyen
*Attorney, Agent, or Firm*—Nikaido Marmelstein Murray & Oram LLP

[57] ABSTRACT

A tube-type sample supplying portion 1 is provided upright above a classification tank 2. A sample inlet pipe 5, which communicating with a culture tank 3, is connected to the lower part of the sample supplying portion 1. An outlet pipe 6, which communicating with the culture tank 3, is connected to the upper part of the sample supplying portion 1. A sample feed pump 4 and a valve 7 are positioned in one of the flow passages between the outlet pipe 6 and the culture tank 3. The flow speed of the fluid including the sample in the sample supplying portion 1 is set to a speed being only a little faster than the final sinking speed of lumps of immature cultivated cells in the fluid.

9 Claims, 7 Drawing Sheets

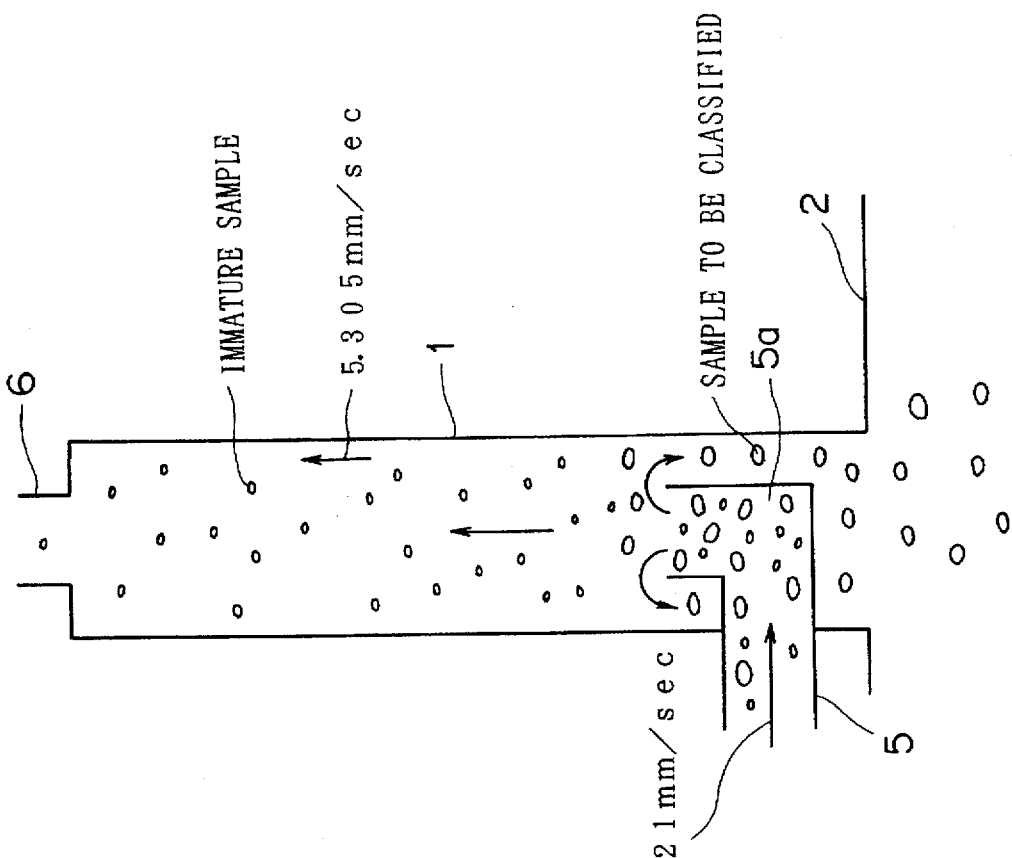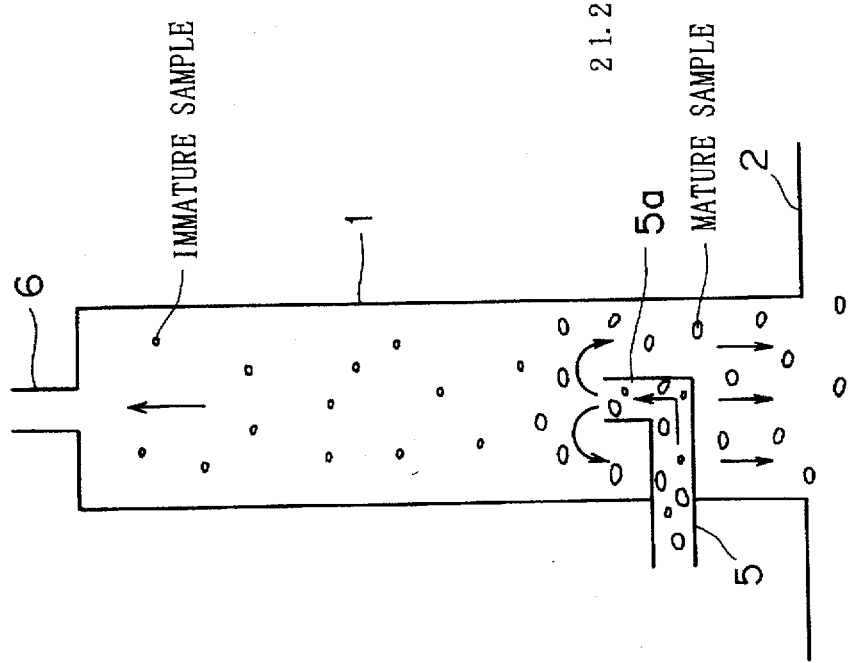

SAMPLE SUPPLY UNIT FOR SETTLING CLASSIFICATION SYSTEM

BACK GROUND OF THE INVENTION

1. Field of the Invention

This invention relates to a sample supply unit for a settling classification system, and more particularly to a sample supply unit that supplies samples to a settling classification system for classifying sample particles by use of the differences in their sinking speeds in a fluid.

2. Description of the Prior Art

In conventional methods for classifying minute objects of powdery particles, for example, it has been known that the objects are classified to make groups being different in size or density by use of the difference in their sinking speeds in a fluid.

For example, the following classification system has been proposed. In the invention disclosed in Japanese Patent No. Hei 3-99, a fluid dispersion including dispersed groups of classifying objects is supplied into a vessel provided, at its bottom, with a piston sliding upward and downward. Then, the piston head in the bottom of the vessel is pushed up to develop an ascending current with no turbulent flows and to overflow the particles having a sinking speed less than the ascending speed from the upper portion of the vessel. Consequently, a precise classification may be enabled.

Further, in the invention disclosed in Japanese Patent Applications Laying-open Nos. Sho 59-196760 and Hei 3178352, by controlling the fluid in density, the objects having a density larger than the fluid density settle in the fluid, while the objects having a density smaller than the fluid density floats, so that the objects are classified to the two groups.

However, most of these methods can only separate the objects to the two groups and can not achieve such a classification as the classification of lumps of cells to each of multi-groups differing in growth phase. Further, they also can not be expected to achieve a classification accuracy being suitable for such objects as lumps of cells, because of a development of turbulent flows in the pipes.

Accordingly, the applicant of the present invention has proposed, in the specification of Japanese Patent Application No. Hei 5-125743, a settling classification system which can classify such classifying objects as lumps of various cells differing in growth phase into multi-groups and, at the same time, can classify a large amount of the objects.

However, in these conventional classification systems, when lumps of cultivated cells are actually classified, the samples have been dropped one by one from the sample introducing port by hand works to classify them. Therefore, there has been a drawback that a large amount of samples only can not be classified instantaneously and continuously but also undesirable bacteria or pollutants may possibly be contaminated because of the hand works.

SUMMARY OF THE INVENTION

The present invention has been achieved to eliminate the above-mentioned drawback. Therefore, it is an object of the invention to provide a sample supply unit for a settling classification system, which can supply continuously a large amount of lumps of cultivated cells in a sterile condition.

The first aspect of the present invention is a sample supply unit for a settling classification system including a tube-type sample supplying portion provided upright above a classification tank of the settling classification system so as to be connected to the upper surface of the classification tank; a sample inlet pipe one end of which is connected to the lower part of the sample supplying portion, the other end of which communicating with a culture tank; an outlet pipe one end of which is connected to the upper part of the sample supplying portion, the other end of which communicating with the culture tank; and a sample feed pump positioned in one of the flow passages of the inlet pipe and the outlet pipe.

The second aspect of the present invention is a sample supply unit for a settling classification system including a tube-type sample supplying portion provided upright above a classification tank of the settling classification system so as to be connected to the upper surface of the classification tank; a sample inlet pipe one end of which is connected to the lower part of the sample supplying portion, the other end of which communicating with both of the first culture tank and the second culture tank; and an air compressor communicating with both of the first culture tank and the second culture tank.

Further, in this case, a changeover means may be provided, which may change over the feed of the compressed air to each of the first culture tank and the second culture tank, and which may change over the feed of a part of the samples supplied from one of the first culture tank and the second culture tank to the sample supplying portion so as to return the samples to the other of the two culture tanks.

In the above-mentioned structure, at the sample supplying portion, the port of the outlet pipe is open preferably downward and the port of the sample inlet pipe is open preferably upward.

Further, the length of the sample supplying portion is preferably not less than triple the inner diameter thereof, and also the distance between the port of the sample inlet pipe and the port of the outlet pipe is preferably not less than triple the inner diameter of the sample supplying portion.

The determined flow rate of the fluid including the samples in the sample supplying portion is preferably a little faster than the final sinking speeds of lumps of immature cultivated cells in the fluid.

The third aspect of the present invention is a sample supply unit for a settling classification system including a tube-type sample supplying portion provided upright above a classification tank of the settling classification system so as to be connected to the upper surface of the classification tank; a stirrer mounted in the sample supplying portion; a valve positioned between the sample supplying portion and the classification tank.

Further, the stirrer is preferably a propeller stirrer, the stirring speed of which is set to a speed that the samples may be homogeneously dispersed in the fluid.

The operations of the above-mentioned aspects of the present invention will be described in the following.

In the first aspect of the present invention, first, the pump is operated to supply samples to the classification tank. When the pump is running, the samples mixed with the fluid in the culture tank are supplied, via the sample inlet pipe, from the under side of the sample supplying portion provided upright above the classification tank of the settling classification system. The fluid is returned to the culture tank via the outlet pipe connected to the upper part of the sample supplying portion. At that time, in the sample supplying portion, the samples with a larger sinking speed than the ascending fluid flow may sink against the fluid flow to come to the classification tank. While, the immature samples with a smaller sinking speed than the ascending fluid flow return to the culture tank via the outlet pipe so as to be cultivated again. Thus, since no hand works are required to supply the samples to the classification tank, it is possible to prevent the contamination of undesirable bacteria or pollutants.

In the second aspect of the present invention, the air compressor is operated to supply the samples into the classification tank. When the air compressor is running, the samples mixed with the fluid in the first culture tank or the second culture tank are supplied, via the sample inlet pipe, from the under side of the sample supplying portion provided upright above the classification tank of the settling classification system.

Further, in this case, by the changeover means, for example, when the samples in the first culture tank are requested to be supplied to the classification tank, the compressed air from the air compressor is supplied into the first culture tank. The samples mixed with the fluid in the first culture tank are supplied, via the sample inlet pipe, from the under side of the sample supplying portion provided above the classification tank of the settling classification system. The fluid is returned to the second culture tank via the outlet pipe connected to the upper part of the sample supplying portion. At that time, in the sample supplying portion, the samples with a larger sinking speed than the ascending fluid flow may sink against the fluid flow to come to the classification tank. While, the immature samples with a smaller sinking speed than the ascending fluid flow return to the second culture tank via the outlet pipe so as to be cultivated again. Besides, if the samples in the second culture tank are supplied to the classification tank by the changeover means, the liquid flow including the immature samples is changed to return to the first culture tank.

In one of the additional aspects of the invention, since, at the sample supplying portion, the port of the outlet pipe is open downward and the port of the sample inlet pipe is open upward, the fluid stream including the samples flows from the under side to the upper side, wherein the samples having a sinking speed larger than a designated speed may sink against the stream to come into the classification tank.

Further, as the length of the sample supplying portion is not less than triple the inner diameter thereof and also the distance between the port of the sample inlet pipe and the port of the outlet pipe is not less than triple the inner diameter of the sample supplying portion, the fluid flow may be easily balanced with the sample sinking speed.

Moreover, since the determined flow rate of the fluid including the samples in the sample supplying portion is a little faster than the final sinking speeds of the lumps of immature cultivated cells in the fluid, the lumps of the mature cultivated cells come into the classification tank, while the lumps of the immature cultivated cells are returned to be cultivated again.

In the third aspect of the present invention, when the stirrer is in operation, the fluid including the samples is stirred, which have been supplied to the tube-type sample supplying portion provided upright above the classification tank of the settling classification system so as to be connected to the upper surface of the classification tank. Then, the valve is opened to deliver the samples into the classification tank.

In one of the additional aspects of the above invention, as the stirrer is a propeller stirrer, the fluid is easily stirred so that the samples may be homogeneously dispersed in the fluid.

BRIEF DESCRIPTIONS OF THE DRAWINGS

FIG. 2 is a schematic diagram showing movements of samples in a sample supplying tank according to this invention FIG. 3 is a schematic diagram showing movements of samples, with practical stream speeds, in a sample supplying tank according to this invention;

Figure 8B:
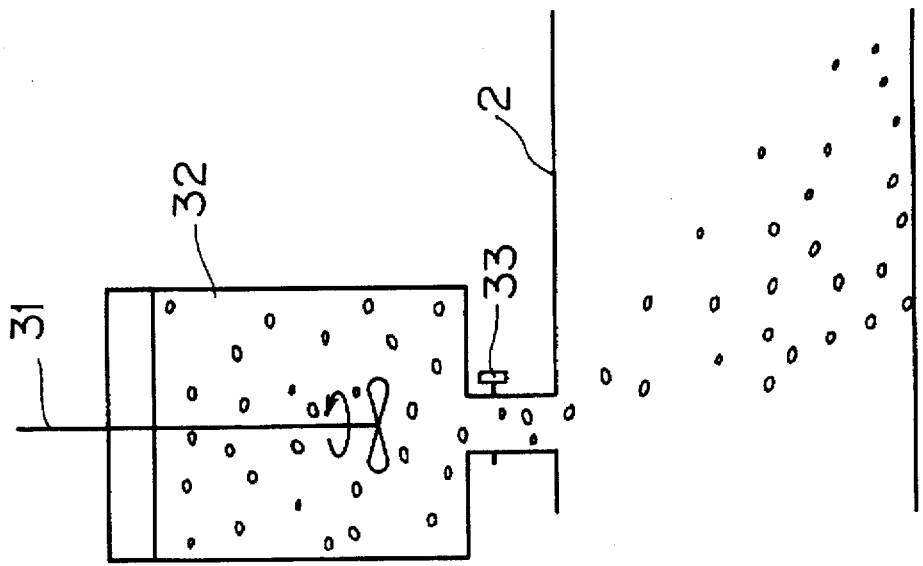
Figure 8A:
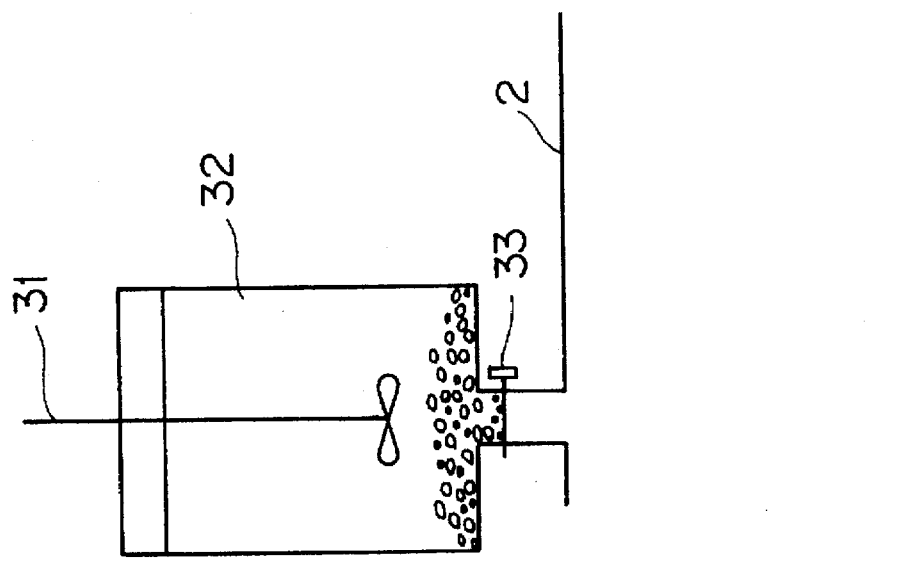
Figure 9A:
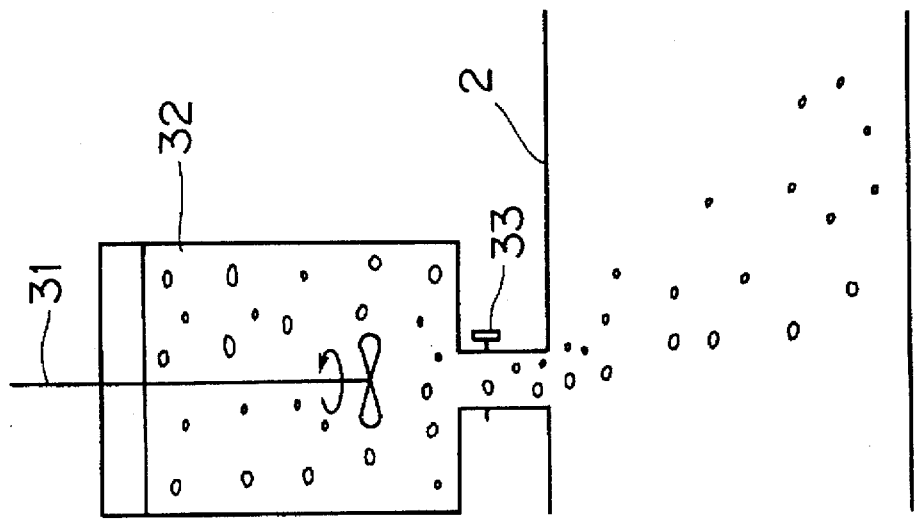
Figure 9B:
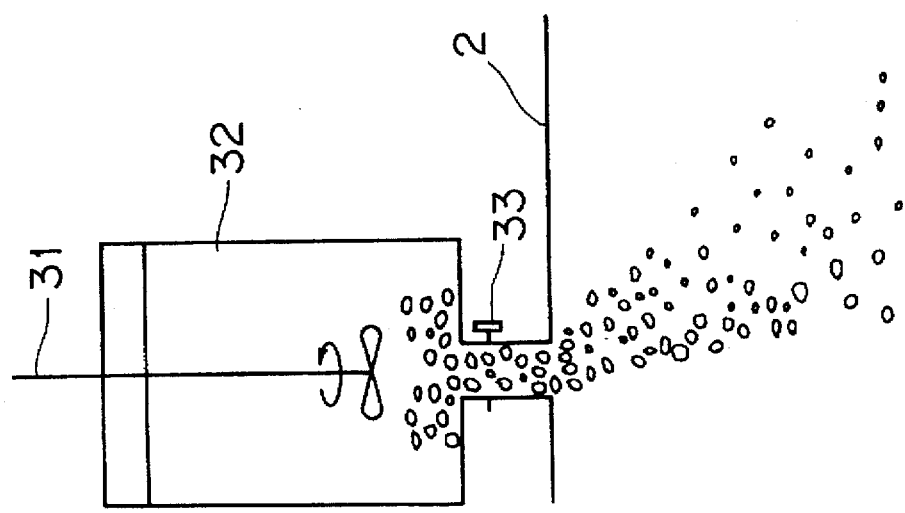

FIG. 8A is a schematic diagram of the third embodiment, which shows the state that the stirrer is stopped and the valve is closed, while FIG. 8B shows the state that the stirrer is in operation and the valve is open; and FIG. 9A is a schematic diagram of the third embodiment, which shows the state that the stirrer insufficiently rotating, while FIG. 9B shows the state that the stirrer is appropriately rotating.

DETAILED DESCRIPTION OF THE PREFERRED EMBODIMENTS

The preferred embodiments of this invention will be explained as referring to the accompanying drawings.

Figure 1:
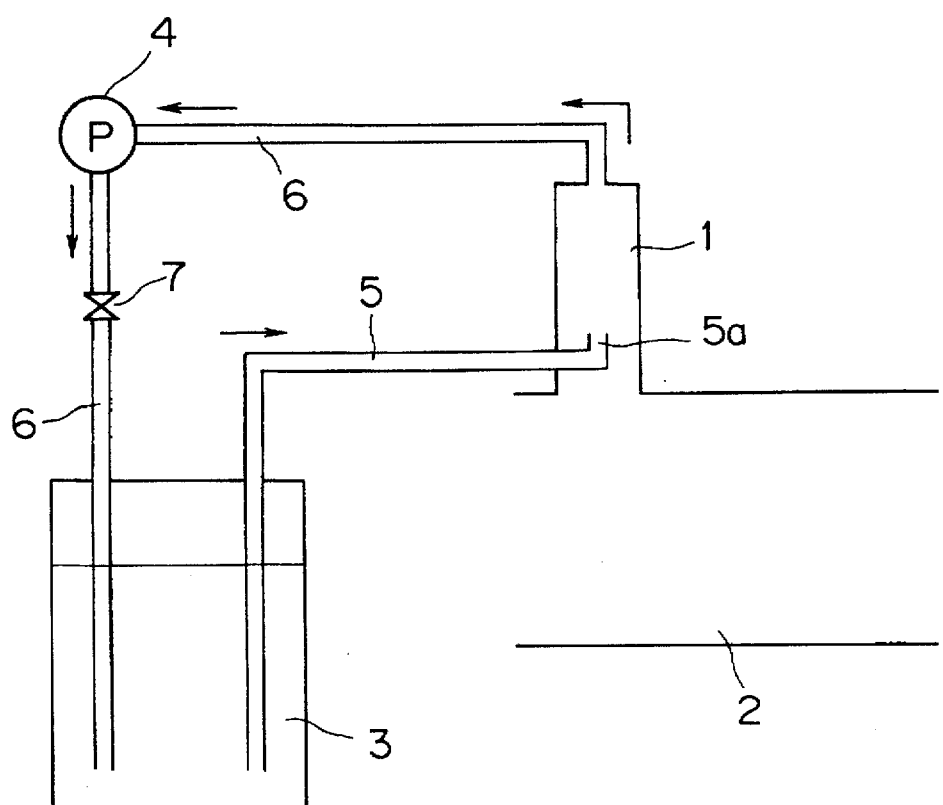
FIG. 1 is a schematic diagram of the first embodiment according to this invention.

FIG. 1 shows the first embodiment of this invention, in which designated 2 is a classification tank of a settling classification system, the classification tank being the same in structure as the one that the applicant of this application has proposed in Japanese Patent Application No. Hei 5-125743.

Above the classification tank 2, a sample supplying portion 1 is provided upright. The sample supplying portion 1 is formed in cylindrical or polygon shape, having a length more than triple its inner diameter.

Further, on the lower side surface of the sample supplying portion 1, a sample inlet pipe 5 is connected. The fore end 5a of the sample inlet pipe 5 protrudes into the sample supplying portion 1 and is bent in L-shape, the port of which is open upward. While, the other end of the sample inlet pipe 5 is immersed into, for example, the cultivation fluid in a culture tank 3, the sample inlet pipe 5 communicating the culture tank 3 with the sample supplying portion 1.

And, the sample inlet pipe 5 is composed of a sterilizable tube, such as a silicon tube, the fore end 5a being made of a stiff material, such as resin or metal.

Further, in the upper side of the sample supplying portion, an outlet pipe 6 is connected, the port of which is open downward. The other end of the outlet pipe 6, via a pump 4 and a flow-rate controlling pinch cock 7, is immersed into the cultivation liquid in the culture tank 3. The outlet pipe 6 and the sample inlet pipe 5 are filled with the same liquid as the cultivation liquid in the culture tank 3.

The outlet pipe 6 is also composed of a such a sterilizable tube as silicon tube. Further, each diameter of the sample inlet pipe and the outlet pipe is about a half to a third of the inner diameter of the sample supplying portion 1.

Next, referring to the operation of this system, the lumps of cells cultivated in the culture tank 3 is supplied under pressure, from the fore end 5a, via the sample inlet pipe 5, with a liquid, such as a cultivation liquid, by the pump 4.

Thus, an upward stream is developed in the sample supplying portion 1, the speed of which is influenced or controlled by the inner diameters of the sample inlet pipe 5/the outlet pipe 6, the sample supplying portion 1, the flow rate of the pump 4, or the flow-rate controlling pinch cock 7. The flow speed of the fluid including the samples in the sample supplying portion is controlled so as to become a little faster than the final sinking speeds of the lumps of immature cultivated cells in the fluid.

Therefore, as shown in FIG. 2, only the immature samples flow upward in the sample supplying portion 1 to flow out into the outlet pipe 6, while, the samples to be classified may sink against the upward stream to come into the classification tank 2. The immature samples having flown out from the outlet pipe 6 are returned to, via the pump 4 and the flow-rate controlling pinch cock 7, to the culture tank so as to be cultivated again.

For example, as shown in FIG. 3, when the inner diameter of the tube-type sample supplying portion 1 is decided to be 20 mm; the inner diameters of the sample inlet pipe 5 and the outlet pipe 6 are 10 mm; and the flow-rate is 0.1 lit./min, the flow rate in the sample inlet pipe leading to the sample supplying portion becomes 21.221 mm/sec. Therefore, all of the lumps of cultivated cells are transferred from the fore end 5a to the sample supplying portion 1 via the sample inlet pipe 5.

While, as the flow speed in the sample supplying portion becomes 5.305 mm/sec, the lumps of the immature cultivated cells with the final sinking speed less than 5.305 mm/sec ascend to enter into the outlet pipe 6 and return to the culture tank 3. The lumps of the cultivated cells to be classified having the other final sinking speed may sink in the sample supplying portion 1 to enter into the classification tank 2 of the settling classification system.

Thus, according to this embodiment of the sample supply unit for the settling classification system, the large amount of lumps of cultivated cells in the culture tank 3 can be supplied, in a sterile condition, to the classification tank 2, wherein only the lumps of the mature cultivated cells to be classified can be delivered.

Next, the preferred second embodiments of this invention will be explained.

Figure 4:
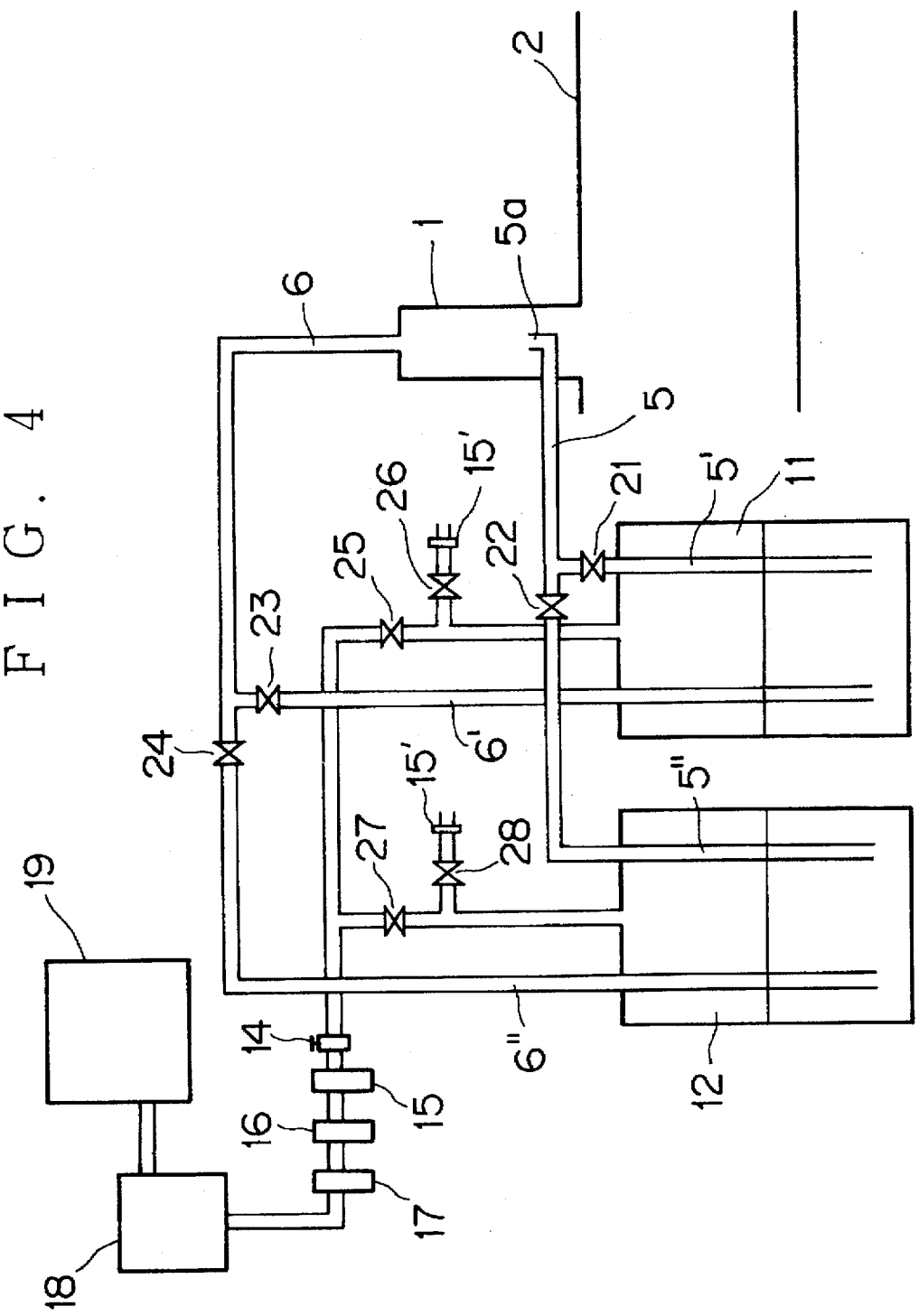
FIG. 4 is a schematic diagram of the second embodiment according to this invention.

FIG. 4 shows the second embodiment of this invention, in which above the classification tank 2, a sample supplying portion 1 is provided upright. The sample supplying portion 1 is formed, similar to the first embodiment, in cylindrical or polygon shape, having a length more than triple its inner diameter.

Further, on the lower side surface of the sample supplying portion 1, a sample inlet pipe 5 is connected. The fore end 5a of the sample inlet pipe 5 protrudes into the sample supplying portion 1 and is bent in L-shape, the port of which is open upward. While, the other end of the sample inlet pipe 5 is branched midway into the first sample inlet pipe 5' and the second sample inlet pipe 5", each of which, via a valve 21 or via a valve 22, is immersed into, for example, the cultivation fluid in the first culture tank 11 or the second culture tank 12.

While, to the upper side of the sample supplying portion 1, an outlet pipe 6 is connected, the port of which is open downward. The other end of the outlet pipe 6 is also branched midway into the first outlet pipe 6' and the second outlet pipe 6", via a valve 23 or via a valve 24, is immersed into the cultivation liquid in the first culture tank 11 or the second culture tank 12.

Further, this sample supply unit is provided with an air compressor 19, the pipe supplying a compressed air from the air compressor 19 is branched into two pipes, each of which communicating with each of the first culture tank 11 or the second culture tank 12, via a valve 25 or 27.

And, in the pipe line supplying the compressed air between the air compressor 19 and the branch portion, there are sequentially provided with an air dryer 18, a main filter 17, a mist separator 16, and a filter 15.

Thus, the compressed air supplied from the air compressor 19 is dried by the air dryer 18, the dust being removed by the main filter 17, further, the contaminated oil being removed by the mist separator 16, and the undesirable bacteria being eliminated, so that the clean air may be obtained.

Further, each of the pipings between the valve 25/27 and the first culture tank 11/the second culture tank 12 has each branch pipe which is open to atmosphere via the valves 26, 28 and via the filters 15', 15'.

Moreover, a changeover means of the invention comprises the valves 21 to 28. The circulating pipings 5, 6, the valves 21 to 24, and the culture tanks 11, 12 are provided with the same liquid as the cultivated liquid in the culture tank.

Next, the operation of this system will be explained in the following.

Figure 5:
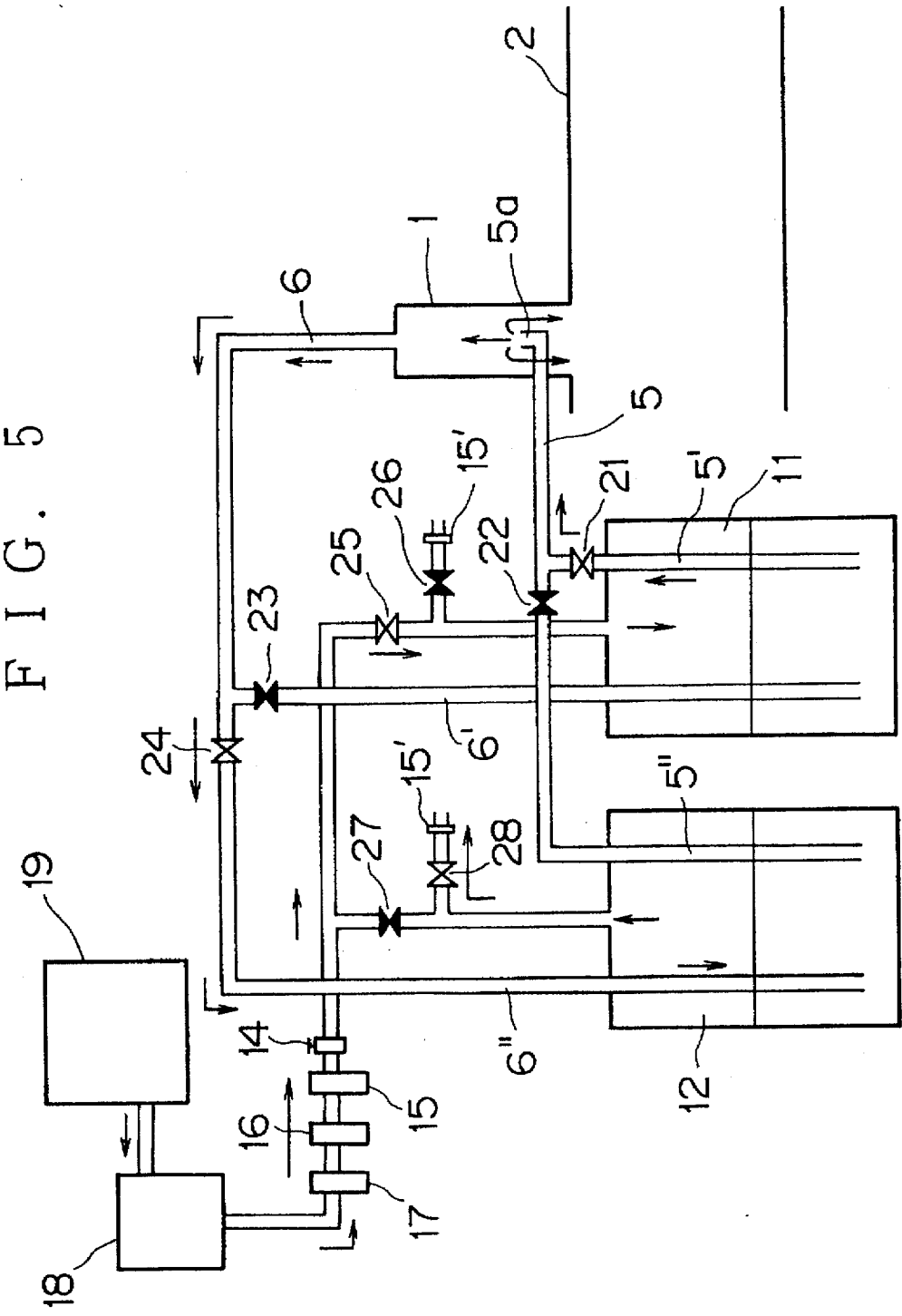
FIG. 5 is a schematic diagram showing the operation of the second embodiment.

First, as shown in FIG. 5, the valves 21,24,25,28 are opened; the valves 22, 23, 26, 27 are closed. By the air compressor 19, the air is supplied into the first culture tank 11 so that the fluid including the samples is supplied under pressure into the sample supplying portion 1.

At that time, an upward stream develops in the sample supplying portion 1. The stream speed in the sample supplying portion 1 is set by a clean regulator 14 to a speed being a little faster than the final sinking speed of the immature cultivated samples not to be classified Therefore, in the sample supplying portion 1, similar to the first embodiment, as shown in FIG.2, the samples to be classified may sink against the upward stream to be delivered into the classification tank 2, while the immature cultivated samples flow out with the fluid from the outlet pipe 6 positioned at the upper part of the sample supplying portion 1.

The fluid including the immature samples flew out from the outlet pipe 6 are returned to, via the valve 24, to the second culture tank 12. The air in the culture tank 12 is exhausted to the atmosphere, via the valve 28 and via the filter 15', according to the ascent of the fluid level.

Figure 6:
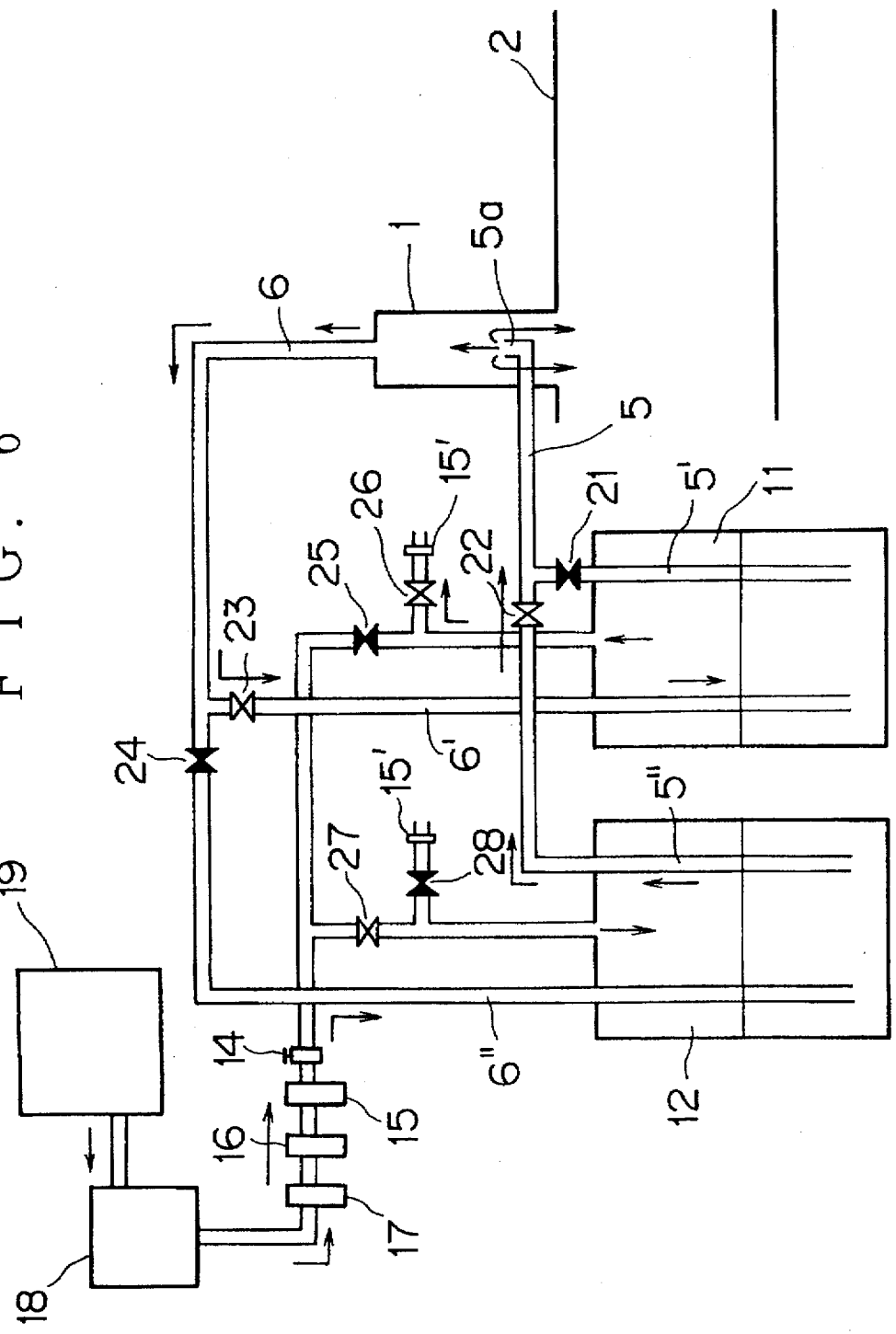
FIG. 6 is a schematic diagram showing the operation of the second embodiment when the culture tanks-to supply the samples have been changed over.

While, in case that the samples in the second culture tank 12 shall be classified, as shown in FIG. 6, to the contrary, the valves 22, 23, 26, 27 are opened; valves 21, 24, 25, 28 are closed; and the air is supplied to the second culture tank 12 by the air compressor 19. Thus, the fluid including the samples in the second culture tank 12 is delivered, under pressure, into the sample supplying portion 1 via the valve 22.

For example, similar to the first embodiment, as shown FIG.3, when the inner diameter of the tube-type sample supplying portion 1 is decided to be 20 mm; the inner diameters of the sample inlet pipe 5/the outlet pipe 6 are 10 mm; and the flow-rate is 0.1 lit./min, the flow rate in the sample inlet pipe leading to the sample supplying portion becomes 21.221 mm/sec. Therefore, all of the lumps of cultivated cells are transferred from the fore end 5a to the sample supplying portion 1 via the sample inlet pipe 5.

While, as the flow speed in the sample supplying portion becomes 5.305 mm/sec, the lumps of the immature cultivated cells with a final sinking speed less than 5.305 mm/sec ascend to enter into the outlet pipe 6 and returns, for example, to the second culture tank 12, wherein the samples are delivered from the first culture tank. The lumps of the cultivated cells to be classified having the other final sinking speed may sink in the sample supplying portion 1 to enter into the classification tank 2 of the settling classification system.

Thus, according to this embodiment of the sample supply unit for the settling classification system, the large amount of lumps of cultivated cells in the culture tank 11 or in the second culture tank 12 can also be supplied, in a sterile condition, to the classification tank 2, wherein only the lumps of the mature cultivated cells can be delivered.

Figure 7:
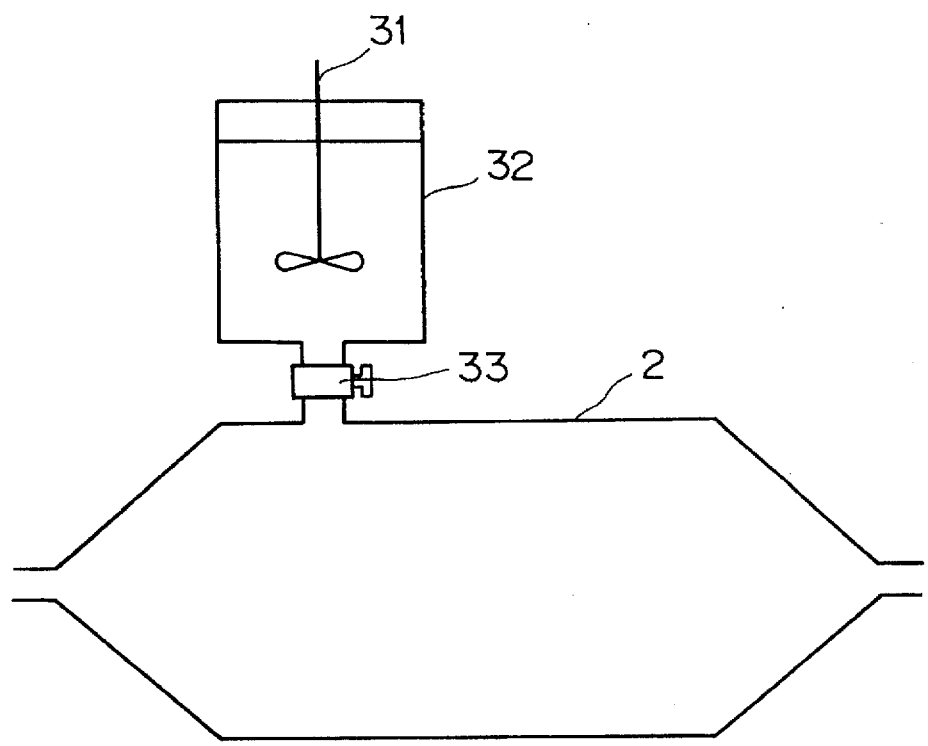
FIG. 7 is a schematic diagram of the third embodiment according to this invention.

Next, the preferred third embodiment of this invention will be explained. FIG.7 shows the third embodiment of this invention.

As shown in the drawing, at a sample inlet port provided in the top of upstream portion of a classification tank 2, an on-off valve 33 such as a ball valve or a sleeve valve is attached. A sample supply tank 32 having a propeller stirrer 31 is positioned and connected to the on-off valve 33 so that the sample supplying tank 32 communicates with the classification tank 2 when the on-off valve 33 is opened.

In this case, the sample supplying tank 32 may be a culture tank itself. The piping from the sample supplying tank 32 to the valve 33 has such a short length that the samples may not accumulate therein. Wherein, the fluid in the sample supplying tank 32 is the same as the liquid in the classification tank 2.

Next, the operation of this system will be explained in the following.

When no classification is carried out, as shown in FIG. 8A, the on-off valve 33 is closed. When the classification is carried out, as shown in FIG. 8B, the stirrer 31 is rotated so that the samples are homogeneously dispersed in the fluid. Then, the on-off valve 33 is opened. The sample is supplied as freely sinking to the classification tank 2.

At that time, when the stirrer rotates with a not less than 100 rpm speed, as shown in FIG. 9B, the samples may sink freely one by one so that the samples are homogeneously dispersed in the fluid. While, when the stirrer rotates with a less than 100 rpm speed, as shown in FIG. 9A, the samples accumulate on the bottom of the sample supplying tank 32 so that the samples sinks as interfering each other, which resulting in that a precise classification can not be surely accomplished.

Also in this embodiment, the large amount of lumps of cultivated cells in the sample supplying tank 32 can be supplied, in a sterile condition, to the classification tank 2.

As mentioned above, in regard to this invention, since no hand works are required to supply the samples to the classification tank, it is possible to prevent the contamination of undesirable bacteria or pollutants.

What is claimed is:

1. A sample supply unit for a settling classification system comprising:

a tube-type sample supplying portion for being positioned upright above a classification tank of said settling classification system so as to be connected to the upper surface of said classification tank;

a sample inlet pipe one end of which is connected to the lower part of said sample supplying portion, the other end of which communicating with a culture tank;

an outlet pipe one end of which is connected to the upper part of said sample supplying portion, the other end of which communicating with said culture tank; and a sample feed pump positioned in one of the flow passages of said inlet pipe and said outlet pipe.

2. A sample supply unit for a settling classification system as claimed in claim 1, wherein, at said sample supplying portion, the port of said outlet pipe is open downward and the port of said sample inlet pipe is open upward.

3. A sample supply unit for a settling classification system as claimed in claim 1, wherein, said sample supplying portion has a length which is not less than triple the inner diameter thereof, and also the distance between the port of said sample inlet pipe and the port of said outlet pipe is not less than triple the inner diameter of said sample supplying portion.

4. A sample supply unit for a settling classification system as claimed in claim 1, wherein, the determined flow rate of the fluid including the samples in said sample supplying portion is only a little faster than the final sinking speeds of lumps of immature cultivated cells in the fluid.

5. A sample supply unit for a settling classification system comprising:

a tube-type sample supplying portion provided upright above a classification tank of said settling classification system so as to be connected to the upper surface of said classification tank;

a sample inlet pipe one end of which is connected to the lower part of said sample supplying portion, the other end of which communicating with both of a first culture tank and a second culture tank;

an outlet pipe connected to the upper part of said sample supplying portion and communicating with said first and second culture tanks; and an air compressor communicating with both of said two culture tanks.

6. A sample supply unit for a settling classification system as claimed in claim 5, wherein, a changeover means is provided, which may change over the feed of the compressed air to each of said two culture tanks, and which may change over the feed of a part of the samples supplied from one of said two culture tanks to said sample supplying portion so as to return the samples to one of said two culture tanks.

7. A sample supply unit for a settling classification system as claimed in claim 5, wherein, at said sample supplying portion, the port of said outlet pipe is open downward and the port of said sample inlet pipe is open upward.

8. A sample supply unit for a settling classification system as claimed in claim 5, wherein, the length of said sample supplying portion is not less than triple the inner diameter thereof, and also the distance between the port of said sample inlet pipe and the port of said outlet pipe is not less than triple the inner diameter of said sample supplying portion.

9. A sample supply unit for a settling classification system as claimed in claim 5, wherein, the determined flow rate of the fluid including the samples in said sample supplying portion is only a little faster than the final sinking speeds of lumps of immature cultivated cells in the fluid.

* * * * *